US008024985B2

(12) United States Patent
Neubauer

(10) Patent No.: US 8,024,985 B2
(45) Date of Patent: Sep. 27, 2011

(54) SYSTEMS AND METHODS FOR EVALUATING MATERIAL FOR PULLING ROLLS

(75) Inventor: Dean Veral Neubauer, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 12/580,422

(22) Filed: Oct. 16, 2009

(65) Prior Publication Data

US 2010/0037701 A1 Feb. 18, 2010

Related U.S. Application Data

(62) Division of application No. 11/888,185, filed on Jul. 31, 2007, now Pat. No. 7,624,646.

(60) Provisional application No. 60/903,735, filed on Feb. 27, 2007.

(51) Int. Cl.
G01N 33/00 (2006.01)
G01N 3/00 (2006.01)
G01N 3/40 (2006.01)
F16C 13/00 (2006.01)

(52) U.S. Cl. ............... 73/866; 73/788; 73/818; 73/32 R; 492/40

(58) Field of Classification Search ............ 73/818, 73/819, 820, 821, 822, 823, 824, 825, 827, 73/794, 796, 798, 788, 790, 857, 866, 32 R; 492/40

See application file for complete search history.

(56) References Cited

U.S. PATENT DOCUMENTS

| 3,334,010 | A | * | 8/1967 | Moore ........................ 162/154 |
| 3,763,533 | A | | 10/1973 | Blom et al. ..................... 29/132 |
| 3,853,525 | A | * | 12/1974 | Gorman ......................... 65/181 |
| 4,248,664 | A | | 2/1981 | Atkinson et al. ............. 162/156 |
| 4,533,581 | A | | 8/1985 | Asaumi et al. ................. 428/64 |
| 5,005,424 | A | | 4/1991 | Markowski ..................... 73/834 |
| 5,948,994 | A | | 9/1999 | Jen et al. ........................ 73/856 |
| 6,896,646 | B2 | | 5/2005 | Kaiser et al. .................... 492/40 |
| 2004/0192526 | A1 | | 9/2004 | Nakayama et al. ............. 492/40 |
| 2007/0042883 | A1 | | 2/2007 | Daily et al. ..................... 492/40 |
| 2009/0293547 | A1 | * | 12/2009 | Heighway ................... 65/370.1 |

FOREIGN PATENT DOCUMENTS

WO WO2005/121034 12/2005
WO WO 2007066145 A1 * 6/2007

* cited by examiner

Primary Examiner — Lisa Caputo
Assistant Examiner — Punam Roy
(74) Attorney, Agent, or Firm — Siwen Chen

(57) ABSTRACT

Disclosed are systems and methods for evaluating the properties of material used in the manufacture of pulling rolls. In one embodiment, a method is provided for aligning plates comprising the material along an axis and compressing the plates to form a cartridge. The plates can be compressed by a piston. The cartridge can be rotated by a motor. In one embodiment, the cartridge, while rotating, is contacted with a cutting surface to produce a surface finish on the cartridge. Properties such as compressibility, recovery and resiliency, and hardness can be measured.

22 Claims, 10 Drawing Sheets

SYSTEMS AND METHODS FOR EVALUATING MATERIAL FOR PULLING ROLLS

CROSS-REFERENCE TO RELATED APPLICATIONS

This is a divisional application of the U.S. patent application Ser. No. 11/888,185 filed on Jul. 31, 2007 now U.S. Pat. No. 7,624,646 and entitled "SYSTEMS AND METHODS FOR EVALUATING MATERIAL FOR PULLING ROLLS" and claims the benefit under 35 U.S.C. §120, which, in turn, claims the benefit of priority under 35 U.S.C. §119(e) of U.S. Provisional Application Ser. No. 60/903,735 filed on Feb. 27, 2007, the contents of both of which are relied upon and incorporated herein by reference in their entirety.

FIELD OF THE INVENTION

The present invention relates to improved methods and systems for evaluating properties of the material used in the manufacture of pulling rolls, which are used in the manufacture of sheet glass. Material properties such as compressibility, recovery and resiliency, and hardness can be measured under the present invention.

BACKGROUND

Recently, significant attention has been focused on televisions and monitors that offer a larger and clearer viewing picture to a viewer. Such large screen devices typically use a large piece of sheet glass for the viewing surface. Pulling rolls are used in the manufacture of this sheet glass to apply tension to the ribbon of glass from which the sheets are formed, and thus to control the nominal sheet thickness. Typically, producing a pulling roll can take several hours. Pulling rolls are typically made from roll material, such as millboard, which is punched to produce disks that are fired and then pressed onto shafts to produce the pulling roll. These pulling rolls are subsequently cut on a lathe to a particular surface finish and are then contoured for installation into machines used in the production of sheet glass. If a pulling roll ultimately fails to meet certain standards for material properties (e.g., hardness), the roll must be taken apart and rebuilt. Because a set of two pulling rolls must be made with a single lot of material, if the material is unacceptable this results in significant losses in time and cost.

Typically, the roll material is purchased according to broad material specifications, but there is no existing means of testing the incoming material under the conditions that it will be under when manufactured into pulling rolls. For example, when extreme pressure is applied to the pulling rolls, the material properties of compressibility, recovery and resiliency are of concern. In addition, the hardness of the material is of concern as a measure of how well the roll will endure thermal conditions and interface with the glass during production. If a lot of millboard material does not meet the desired specifications, this failure will be unknown until the pulling rolls have been manufactured and put to use. This results in significant losses in both time and cost.

Thus, there is a need in the art for methods and systems for evaluating the properties of material to be used in the manufacture of pulling rolls prior to the production of these pulling rolls.

SUMMARY OF THE INVENTION

The present invention provides systems and methods for evaluating the properties of material that is used in the manufacture of pulling rolls. In accordance with various embodiments, the material properties may be evaluated prior to the pulling rolls being produced. In various embodiments, a tester cartridge is manufactured from the material and properties such as compressibility, recovery and resiliency, and hardness can be measured.

In one embodiment, a method is provided for evaluating the properties of material and comprises aligning a plurality of plates comprising the material along an axis and applying a compressive force along the axis to form a compressed cartridge.

In one embodiment, the plates are formed from a single lot of material. In one embodiment, the cartridge is put into contact with a cutting surface in order to provide a surface finish on the cartridge.

In yet another embodiment, a system for evaluating a cartridge is provided and comprises a piston for transferring a compressive load to at least a portion of the cartridge and means for rotating the cartridge about an axis. In one embodiment, the system comprises a means for quantifying the compressive load. In yet another embodiment, the system comprises means for finishing the exterior surface of the cartridge.

Additional embodiments of the invention will be set forth, in part, in the detailed description, and any claims which follow, and in part will be derived from the detailed description, or can be learned by practice of the invention. It is to be understood that both the foregoing general description and the following detailed description are exemplary and explanatory only and are not restrictive of the invention as disclosed and/or as claimed.

BRIEF DESCRIPTION OF THE DRAWINGS

The accompanying drawings, which are incorporated in and constitute a part of this specification, illustrate certain aspects of the instant invention and, together with the description, serve to explain, without limitation, the principles of the invention.

DETAILED DESCRIPTION OF THE INVENTION

Figure 1A:
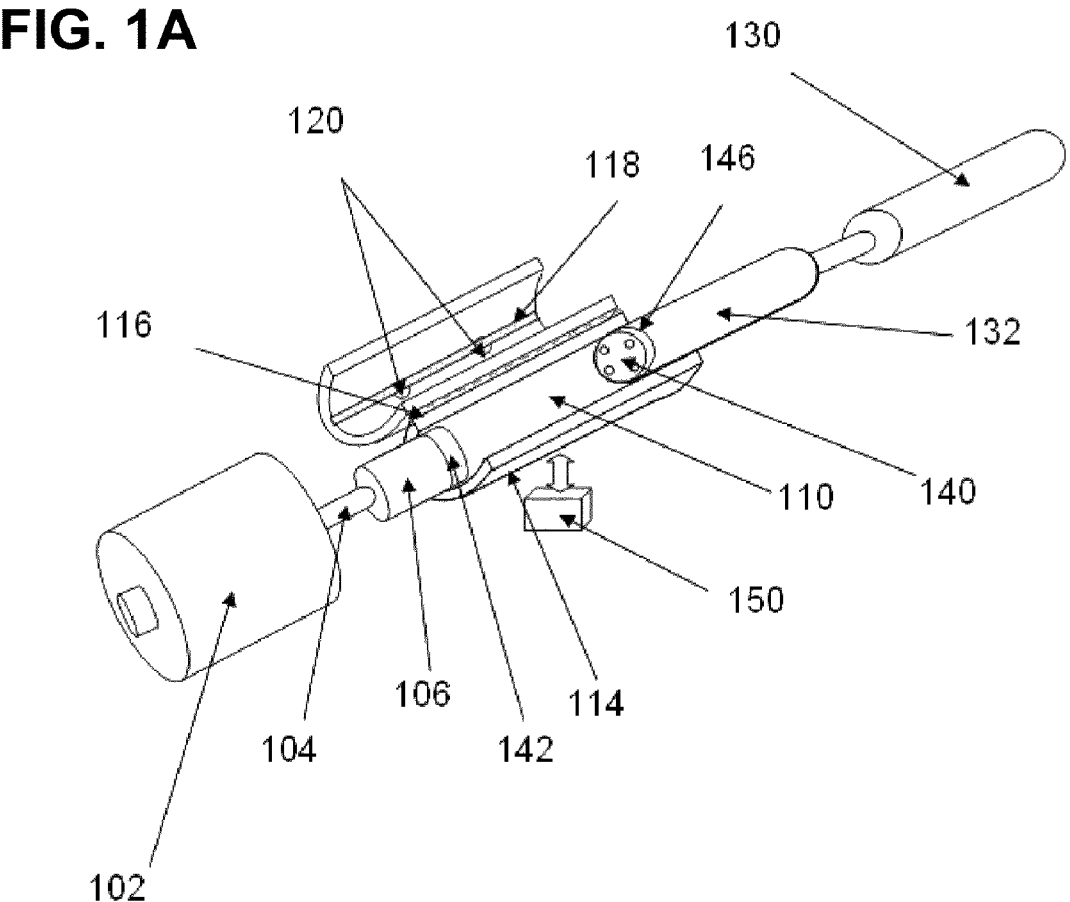
FIG. 1A is a schematic perspective view of a system for forming and testing a cartridge, according to one embodiment of the present invention.

The following description of the invention is provided as an enabling teaching of the invention in its best, currently known embodiment. To this end, those skilled in the relevant art will recognize and appreciate that many changes can be made to the various embodiments of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes embodiments having two or more such "plates" unless the context clearly indicates otherwise.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As briefly summarized above, the present invention provides systems and methods for evaluating the properties of material that is used in the manufacture of pulling rolls, prior to the pulling rolls being produced.

In one embodiment, the present invention provides a system for forming a compressed cartridge comprising plates of millboard material and evaluating the material properties of the cartridge. For example, with reference to FIG. 1A, one embodiment of a system 100 comprises a piston 132 for compressing the cartridge and a means for rotating the cartridge, such as a motor 102. As may be appreciated, the piston is configured to move along a substantially linear path. For example, the piston can move between a first position, in which no compressive load is transferred to the cartridge, and a second position, in which a compressive load is transferred to at least a portion of the cartridge. In other embodiments, the system can also comprises a housing 110, a vacuum cleaning system, at least one anvil, and/or a thrust bearing 146.

In one embodiment, a motor shaft 104 extends from the motor 102 along a longitudinal axis and rotates about this axis. The distal end of the motor shaft 104 may contact one end of the cartridge and thereby rotate the cartridge. In one embodiment, a motor shaft adapter 106 may be positioned at the distal end of the motor shaft 104. The motor shaft adapter may be needed if the motor shaft is of a different size (i.e., having a smaller or larger diameter) than the anvil surface.

In another aspect of the system, a hydraulic cylinder 130 is configured for selectively compressing the cartridge. In various embodiments, the hydraulic cylinder 130 is selectively movable and is coupled to the piston 132 at a first end of the piston. In operation, a second end of the piston can be configured to contact one end of the cartridge. In other embodiments, the second end of the piston 132 may be connected to a thrust bearing 146, which allows the cartridge to spin under the motor's 102 movement but prevents the piston 132 and hydraulic cylinder 130 from consequently spinning. In some embodiments, a thrust bearing is connected to the hydraulic cylinder. In one embodiment, the hydraulic cylinder comprises a force gauge 134 for quantifying the compressive load on the cartridge. In other embodiments, other gauges or devices for measuring or quantifying the load on the cartridge are provided.

Figure 1B:
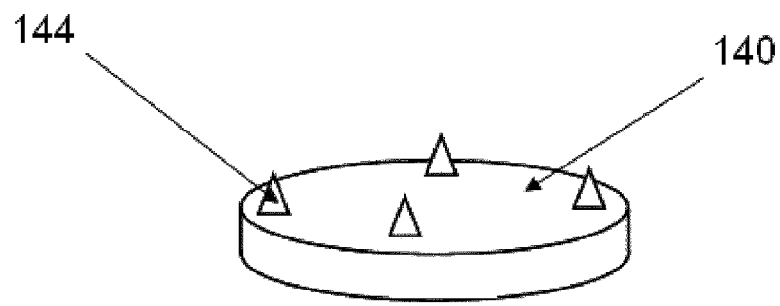
FIG. 1B is a perspective view of an exemplary anvil element of the system as shown in FIG. 1A, according to one embodiment of the present invention.
Figure 2:
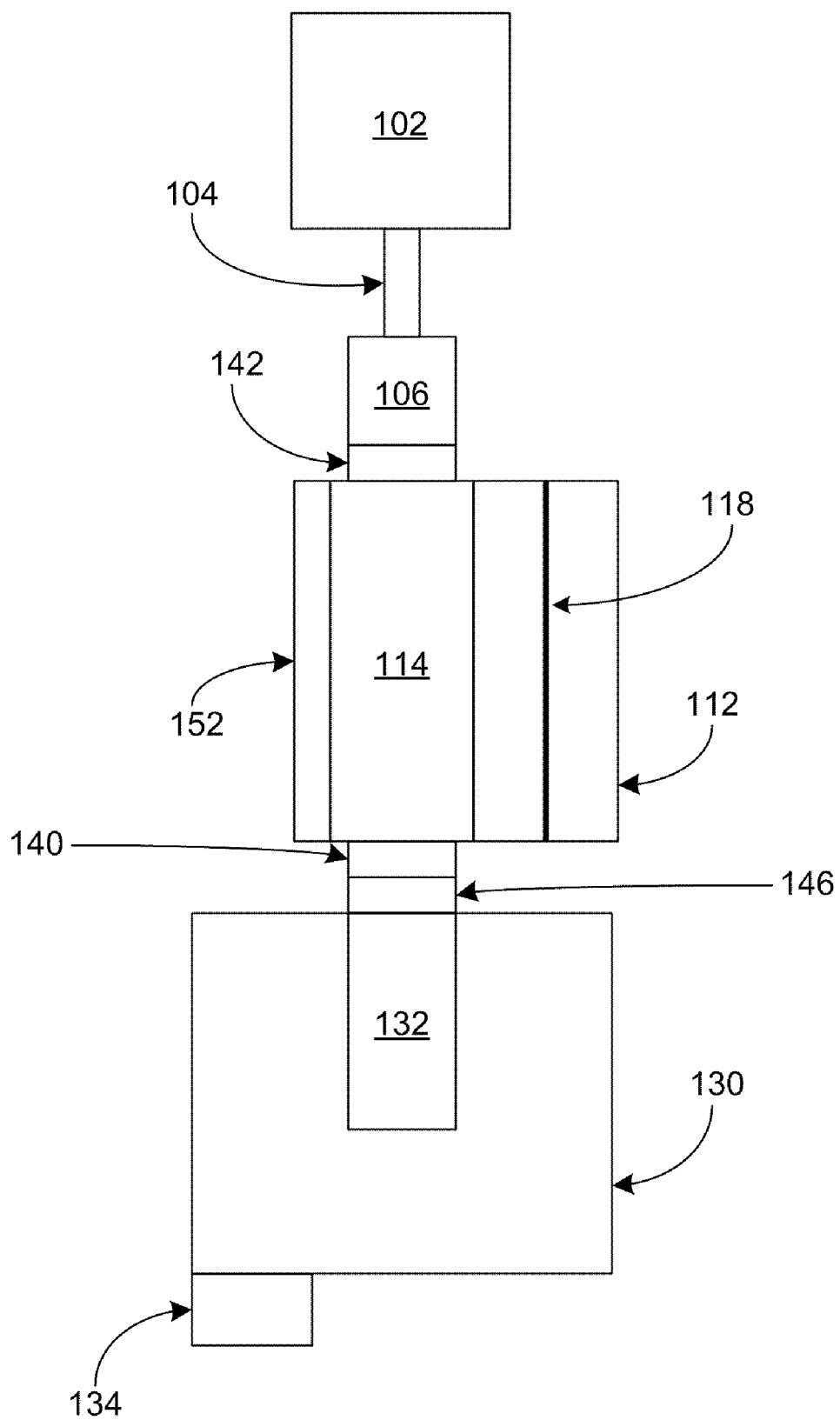
FIG. 2 is a schematic top elevational view of a system for forming and testing a cartridge, according to another embodiment of the present invention.

In one embodiment, at least one anvil is used to grip the cartridge while it is under compression and rotating. For example, as exemplified in FIG. 1A, a first anvil 140 may be interposed between an end of the piston 132 and a first end of the cartridge. The first anvil 140 may comprise one or more indenter cones 144, as shown in FIG. 1B, for gripping the cartridge and preventing slippage. A second anvil 142 may be interposed between a second end of the cartridge and the motor shaft adapter 106. The second anvil 142 may also comprise one or more indenter cones 144 as described above. Some embodiments of the system may include both a first and second anvil. In other embodiments, it is contemplated that the system may comprise either the first anvil or the second anvil, or neither or the respective anvils.

Similarly as described above, a thrust bearing 146 may be interposed between the second end of the piston 132 and the first anvil 140, such that the first anvil 140 will rotate along with the cartridge without transferring the rotational force to the piston. Thus, in some embodiments, one end of the cartridge is in contact with the distal end of the motor shaft 104, while the other end of the cartridge is in contact with the second end of the piston. In other embodiments, an anvil as described above may be positioned in between the cartridge and either or both of the motor shaft and the piston. Additionally as described above, it is contemplated that the thrust bearing may be positioned between the cartridge and the piston, alone, or in combination with an anvil.

In various embodiments, the system comprises a housing 110. In one embodiment, the housing 110 is elongated and comprises a lid 112 and a tray 114. The lid and base may be connected by a hinge 116 to allow the housing to move between a first housing position, in which the at least a portion of the housing (e.g., the housing lid 112) is positioned adjacent the cartridge, and a second housing position, in which at least a portion of the housing (e.g., the housing lid 112) is spaced apart from the cartridge. In some embodiments, the housing may comprise a tray which holds the cartridge (or plurality of plates). The tray can be raised and lowered, such as by a solenoid 150. For example, the tray may be in the "up" position when loading the plates into the housing, and is then lowered while the plates are compressed into the cartridge. The housing may also comprise a ruler 152, or other measuring device, for measuring the length of the cartridge within the housing 110. In other embodiments, the ruler may be positioned separately from the housing. The system may also comprise one or more vacuum ports in communication with the housing 110, for use with the vacuum cleaning system (described in further detail below). For example, as shown in FIG. 1A, two vacuum ports 120 may be positioned along the lid 112 of the housing 110.

In various embodiments, the system comprises a means for finishing the exterior surface of the cartridge. For example, the housing 110 may comprise a cutting surface 118. Other surface finishers may be used, such as devices that sand, buff, cut, or otherwise finish the surface. In an exemplary aspect, the cutting surface 118 can comprise a blade that is connected to the lid 112 and extends along the lid 112 in a direction substantially parallel to the longitudinal axis of the housing 110. In this aspect, the cutting surface 118 extends in a direction substantially parallel to the longitudinal axis of the cartridge when the cartridge is within the housing 110.

As described above, the housing is configured to be positionable around the cartridge. As a result, the cutting surface 118 is positionable between a first non-contact position, in which the cutting surface 118 is spaced apart from the peripheral exterior surface of the cartridge, and a second contact position in which at least a portion of the cutting surface 118 is in contact with the peripheral exterior surface of the cartridge. In one embodiment the cutting surface 118 is positionable to a third contact position, in which the cutting surface is in contact with at least a portion of the peripheral exterior surface of the cartridge. In one embodiment, the third position is configured to form a cartridge having a predetermined radius. In other embodiments, the cutting surface may be positioned elsewhere in the system, rather than as part of the housing. For example, in one embodiment, the system may not include the housing, and the cutting surface may be positioned adjacent the cartridge by other means in order to finish the surface of the cartridge. In one exemplary aspect, the hinge 116 can comprise a tension hinge that is configured to close more slowly as the hinge is lowered into contact with the cartridge so that the cutting surface is prevented from digging into the cartridge and jamming.

In some embodiments, the system 100 also comprises a vacuum cleaning system. As the cutting surface 118 cuts or shapes the cartridge, a dust of particles is often produced. The vacuum cleaning system may be used to remove these particles from the area surrounding the cartridge (e.g., the area within the housing). In one embodiment, the vacuum cleaning system can comprise one or more vacuum ports (e.g., vacuum ports 120 disposed within the lid 112 of the housing 110), one or more air-lines connected to the one or more vacuum ports, an air source, an air regulator, a shut-off valve and a vacuum system for disposal of the particles (e.g., a shop vacuum or dust collector), which is connected to the other end of the air-lines. In other embodiments, the vacuum system comprises one or more hoses exterior to the housing that collect dust or other particles during the finishing or cutting of the cartridge surface.

In one embodiment, the present invention provides a method for evaluating the properties of material used in the manufacture of pulling rolls. In one embodiment, the process comprises providing a plurality of plates that are formed from the material to be tested (e.g., millboard material). In one aspect, the plurality of plates comprises a large enough number of test samples for acceptance sampling of lot material for each roll. For example, and as one skilled in the art will appreciate, under Mil-Std-414 or ANSI/ASQC Z1.9, if a lot size, i.e., the number of disks needed to made a roll, were in the range of 800-1300 disks, the sample size requirement for single sampling under normal instruction criterion would be approximately 30-35 disks. In another aspect, the plates are aligned coaxially along a common longitudinal axis to form a cartridge and are compressed under an applied force acting along the longitudinal axis to form a compressed cartridge. In one embodiment, the plates are aligned within the tray 114 of the housing 110. In this aspect, the base is configured for receipt of the plurality of plates, i.e., the statistically-based sample size of the plates.

The aligned plates are then compressed under the force of the hydraulic cylinder 130 and piston 132, against the resistance of motor shaft adapter 106. In one aspect, the hydraulic cylinder and piston is configured to apply a compressive force between about 50 to about 15,000 psi, alternatively between about 100 to about 12,500 psi, and more preferably between about 100 to about 10,000 psi. In another aspect, the pressure gauge is configured to measure the applied pressure over at least the range of compression. In this aspect, the pressure gauge can also have an identified warning zone if the pressure being applied exceeds a predetermined safety pressure. As described above, anvils that are configured to grip the plates on the ends of the cartridge may be interposed between the piston and the plates, and the motor shaft adapter and the plates, to prevent slippage.

In a further aspect, the compressive force applied to the cartridge can be pre-determined. For example, the compressive force may need to mimic the force that will be applied to a pulling roll in the pulling roll fabrication process. Using an analogous pressure on the cartridge substantially ensures that the cartridge is being made in the same manner as a production pulling roll; thus the material properties of the cartridge will be substantially the same as those of a production pulling roll made of the same material. In one embodiment, the cartridge is compressed to a compressed length under a pre-determined compressive force. The ruler 152 is used to measure the pre and post compression length of the cartridge. It is contemplated that a predetermined number of plates can be used when forming the cartridge.

In accordance with another embodiment, the cartridge is compressed to a predetermined bulk density, and the compressive force required to achieve that bulk density can then be quantified. In some embodiments, the desired predetermined bulk density can be achieved by calculating the predetermined compressed length necessary to achieve the predetermined bulk density (see Example 6, below). In various embodiments, the desired bulk density is from about 0.95 g/cc to about 1.05 g/cc (e.g., 1.00 g/cc). In various other embodiments, the desired bulk density is from about 0.9 g/cc to about 1.20 g/cc.

As may be appreciated by one skilled in the art, disks of millboard material are used in the production of the pulling rolls. Typically, the disks have a center portion that is removed in order to mount the disks on a shaft. In various embodiments of the present invention, the plates used to form the compressed cartridge comprise the punched-out portion, i.e., the center portion, of the disks used to form production pulling rolls. Thus, in some embodiments the plates comprise the same or substantially similar dimensions. In some embodiments the plates are circular, and the compressed cartridge is substantially cylindrical.

In some embodiments, the plurality of plates is provided from a single lot of millboard material (or other material used to produce pulling rolls). In use, pulling rolls are used in pairs and both rolls must be fabricated from a single lot of millboard material. When the plurality of plates is selected from a single lot of millboard material, the evaluated material properties of the compressed cartridge will be analogous to those of the pair of production pulling rolls that are formed from the same lot of material. In various embodiments, the plates that form the millboard material are fired prior to forming the compressed cartridge. In other embodiments, the plates formed from the millboard material are unfired.

According to various embodiments, the compressed cartridge is rotated about its longitudinal axis. In one embodiment, the cartridge is rotated when it is under at least a minimal compressive force. A cutting surface, such as the exemplified cutting surface 118 described above, is configured to contact at least a portion of an external peripheral surface of the cartridge. In one aspect, at least a portion of the peripheral surface of the cartridge can be cut or shaped to achieve a desired finished surface. In another aspect, at least a portion of the peripheral surface of the cartridge can be cut or shaped to a desired dimension, for example and without limitation, a desired diameter.

In one embodiment, the cutting surface may be angled relative to the cartridge to provide a desired surface finish, such as an angle between about 0°, which is substantially parallel to the tangent of the cartridge, to about 90°, which is substantially perpendicular to the tangent of the cartridge. For example and without limitation, the cutting surface may be at an angle of about 30° relative to the cartridge.

In some embodiments, the cartridge may be rotated at a specific rotational speed in order to achieve an adequate surface finish for accurate hardness testing. In one embodiment, the speed is from between about 500 to about 1,500 rpm, alternatively between about 600 to about 1000 rpm, and preferably, between about 700 rpm to about 900 rpm (e.g., 800 rpm). In some embodiments, a combination of an angled cutting surface and a specific rotational speed can be used to achieve an adequate cartridge surface, such as, for example and not meant to be limiting, a combination of the angle of the cutting surface of between about 25° to about 35° and the rotation of the cartridge between about 700 to about 900 rpm. After a desired surface is achieved, a durometer hardness value for at least a portion of the external surface of the cartridge can be determined. In some embodiments, the hardness of at least a portion of the cartridge is measured according to the Shore D hardness test. In other embodiments, the Shore A hardness test, Rockwell hardness test, or other hardness test may be used. As described above, the vacuum cleaning system can be used during or after the process of cutting the cartridge in order to remove the dust of fine particles produced during this process.

Lastly, it should be understood that while the present invention has been described in detail with respect to certain illustrative and specific embodiments thereof, it should not be considered limited to such, as numerous modifications are possible without departing from the broad spirit and scope of the present invention as defined in the appended claims.

EXAMPLES

To further illustrate the principles of the present invention, the following examples are put forth so as to provide those of ordinary skill in the art with a complete disclosure and description of how the ceramic articles and methods claimed herein can be made and evaluated. They are intended to be purely exemplary of the invention and are not intended to limit the scope of what the inventors regard as their invention. Efforts have been made to ensure accuracy with respect to numbers (e.g., amounts, temperatures, etc.); however, some errors and deviations may have occurred. Unless indicated otherwise, parts are parts by weight, temperature is degrees C. or is at ambient temperature, and pressure is at or near atmospheric.

Example 1

Pulling Roll Life vs. Fired Bulk Density

Figure 3A:
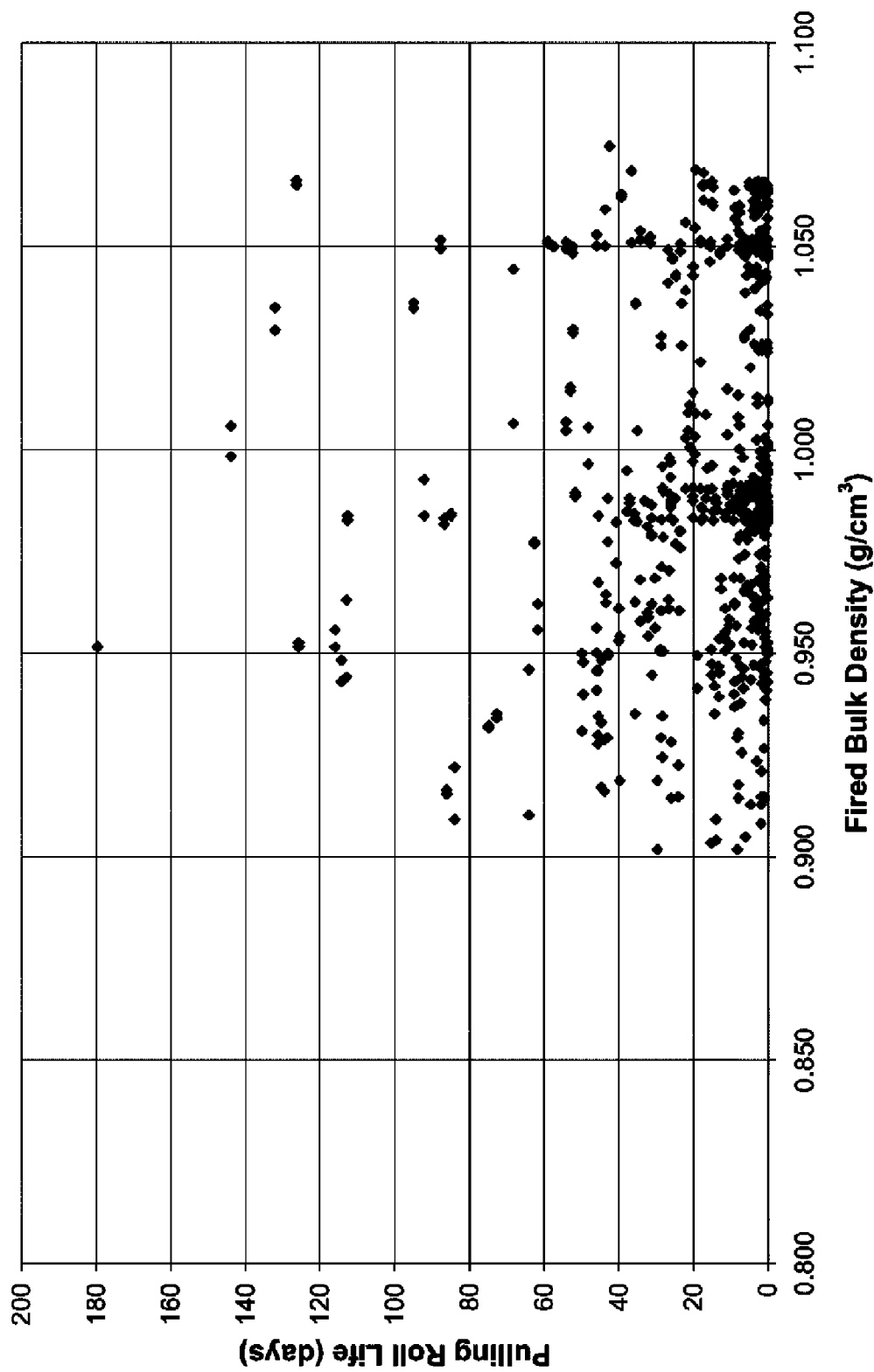
FIG. 3A is a graphical illustration of the life of a pulling roll versus the fired bulk density for exemplary shorter length pulling rolls.
Figure 3B:
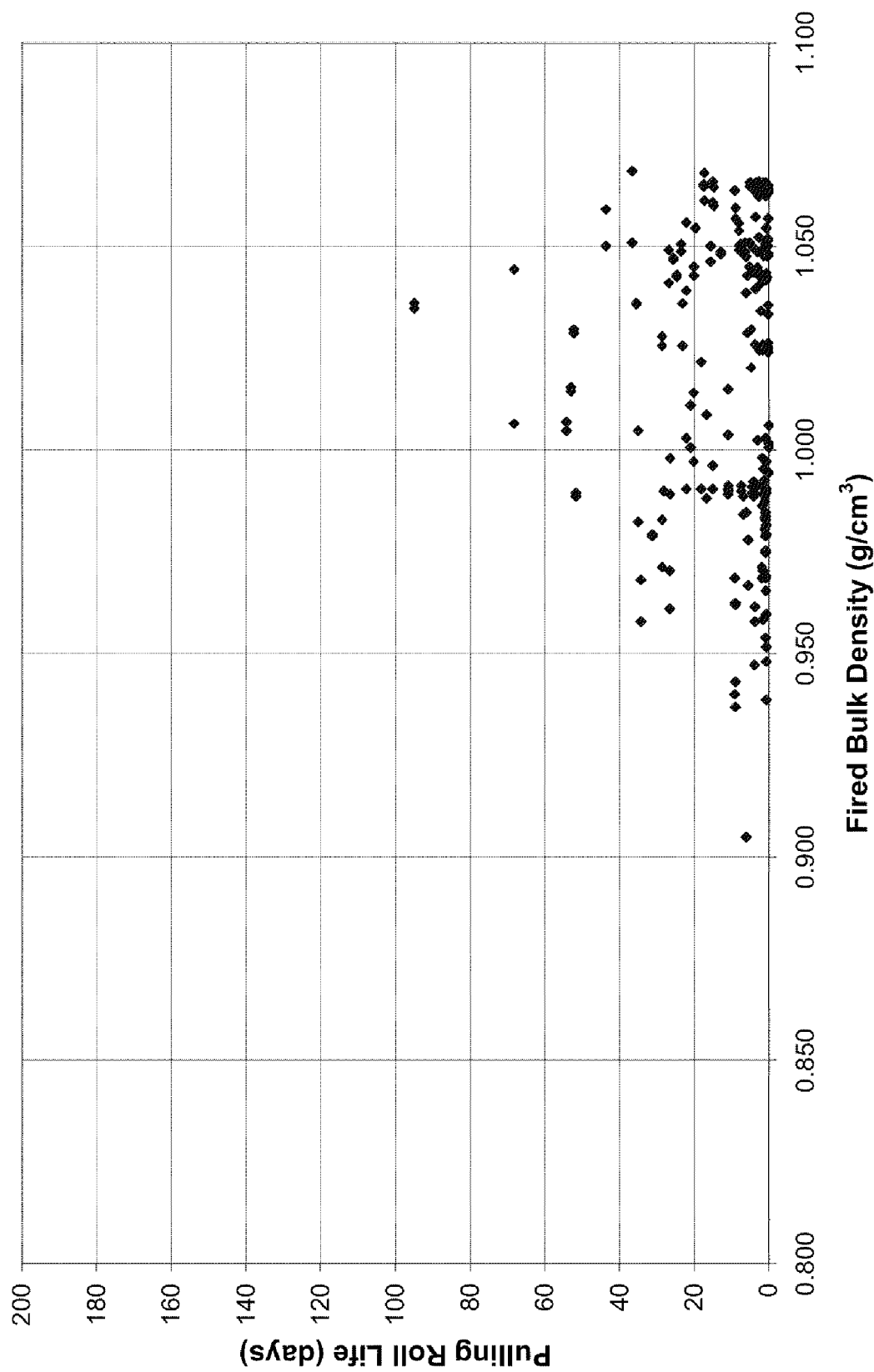
FIG. 3B is a graphical illustration of the life of a pulling roll versus the fired bulk density for exemplary longer length pulling rolls.

Tests were conducted on numerous pulling rolls of different lengths (shorter length, as shown in FIG. 3A, and longer length, as shown in FIG. 3B) to determine what level of fired bulk density correlates to the best pulling roll life (measured in days). As can be seen in FIG. 3A, optimal roll life for a shorter length pulling roll can be achieved when the bulk density is from about 0.95 g/cc to about 1.05 g/cc. As can be seen in FIG. 3B, optimal roll life for a longer length pulling roll can be achieved when the bulk density is from about 1.00 to about 1.05 g/cc.

These bulk density values can be used when preparing a tester cartridge. For example, a tester cartridge can be prepared to simulate a shorter length pulling roll. In order to measure the properties of the millboard material, the cartridge may be compressed to achieve a bulk density of about 0.95 g/cc to about 1.05 g/cc. The material properties measured after compressing the cartridge will be substantially analogous to the properties of the same material when used in production of the shorter length pulling roll.

Example 2

Pulling Roll Life vs. Average Shore D Durometer Hardness

Figure 4A:
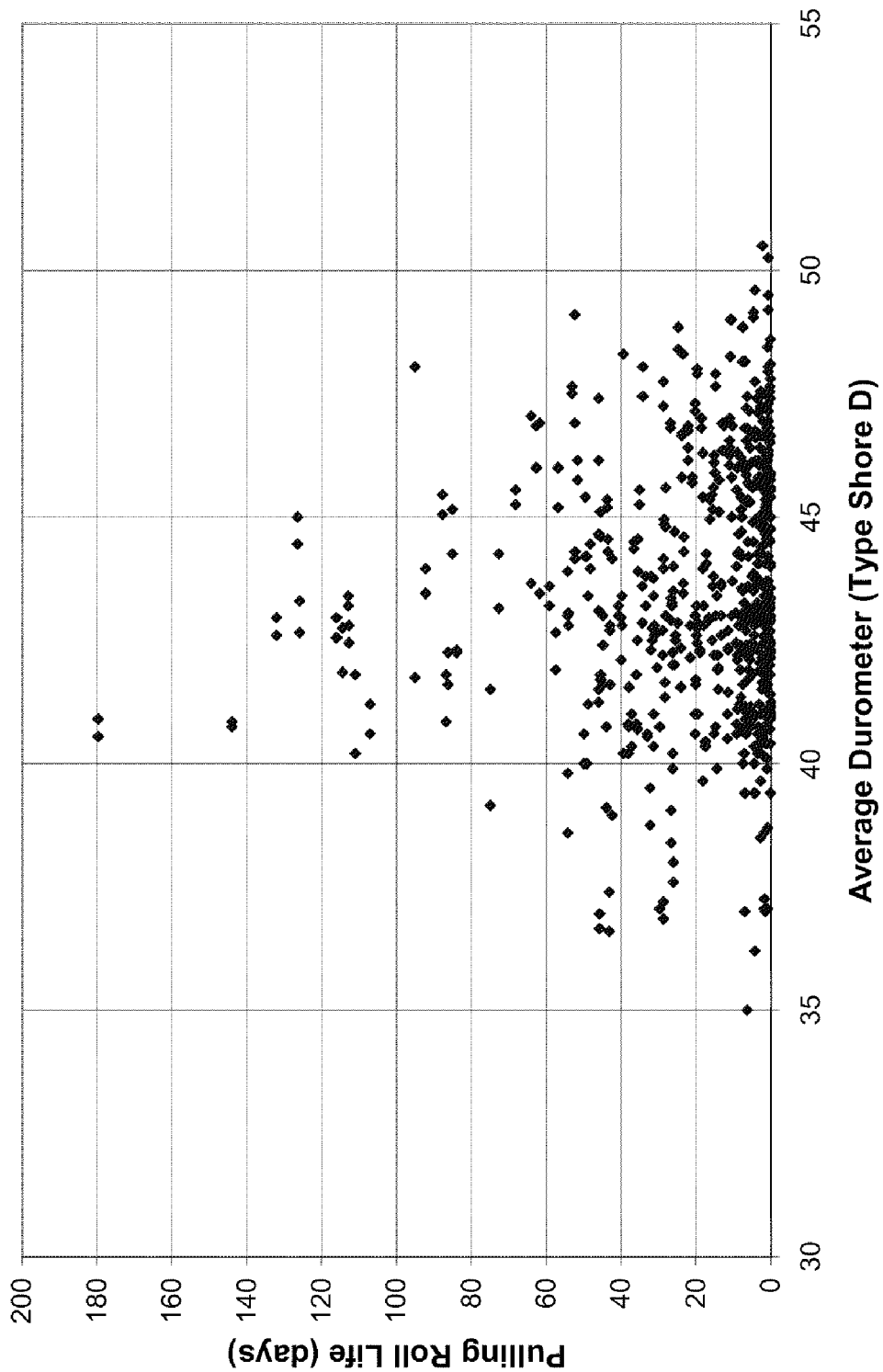
FIG. 4A is a graphical illustration of the life of a pulling roll versus the average durometer hardness value for exemplary shorter length pulling rolls.
Figure 4B:
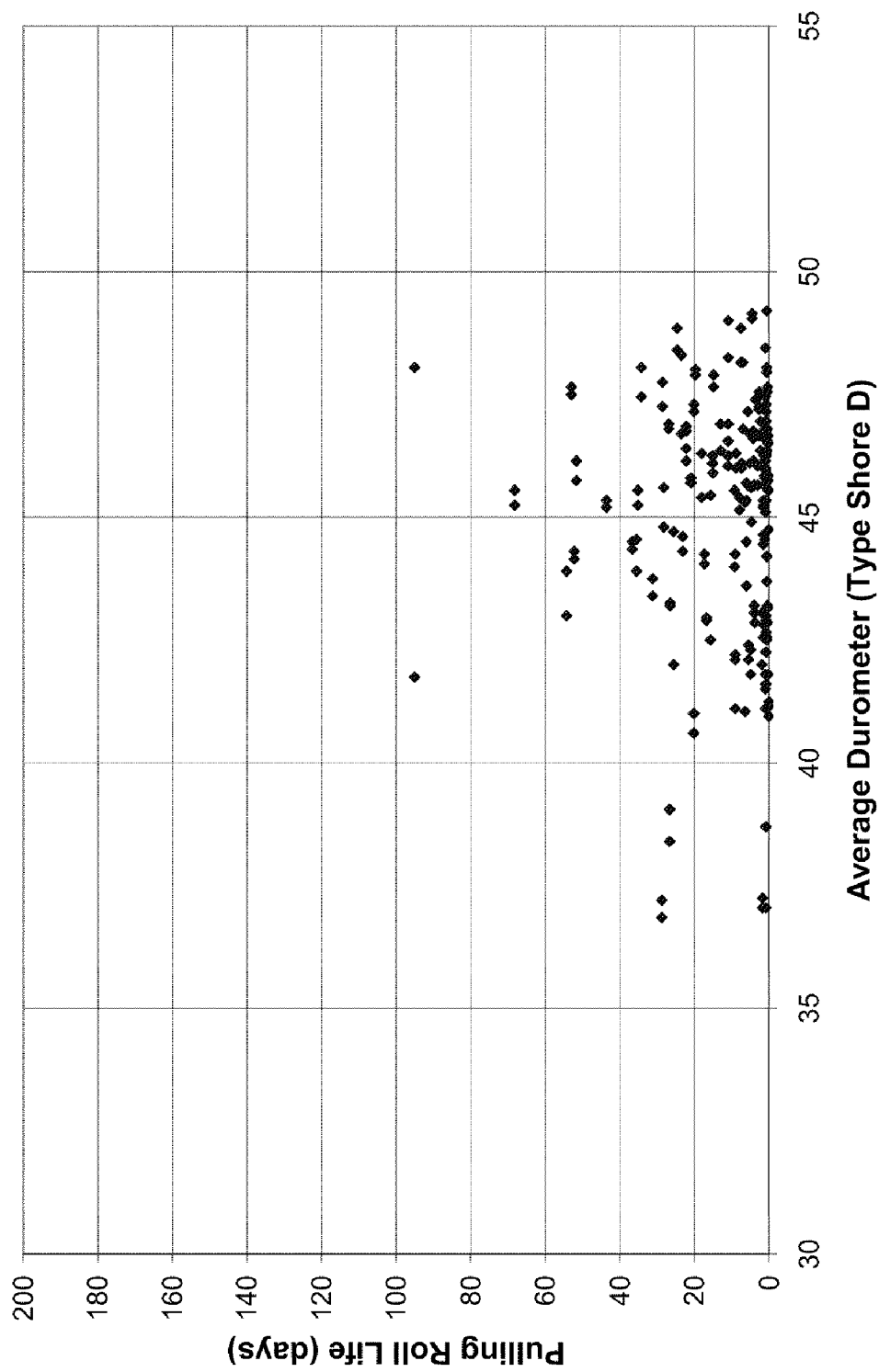
FIG. 4B is a graphical illustration of the life of a pulling roll versus the average durometer hardness value for exemplary longer length pulling rolls.

Tests were conducted on numerous pulling rolls of different lengths to determine the correlation between hardness of a pulling roll and the life (measured in days) of the pulling roll. For these tests, hardness was measured using the Shore D durometer hardness scale. As can be seen in FIG. 4A, optimal roll life for a shorter length pulling roll occurs when the roll has a hardness value from about 40 to about 45. As can be seen in FIG. 4B, optimal roll life for a longer length pulling roll occurs when the roll has a hardness value from about 40 to about 50.

In one aspect, knowledge of optimal durometer levels for finished rolls can provide a metric for evaluating lots of millboard material and their suitability for production of pulling rolls. For example, a tester cartridge comprising plates of one lot of millboard material can be compressed into a cartridge and surface finished as described above. The Shore D durometer hardness of portions of the cartridge can be measured and compared to the optimal durometer levels shown in FIGS. 4A and 4B, for example.

Example 3

Figure 5A:
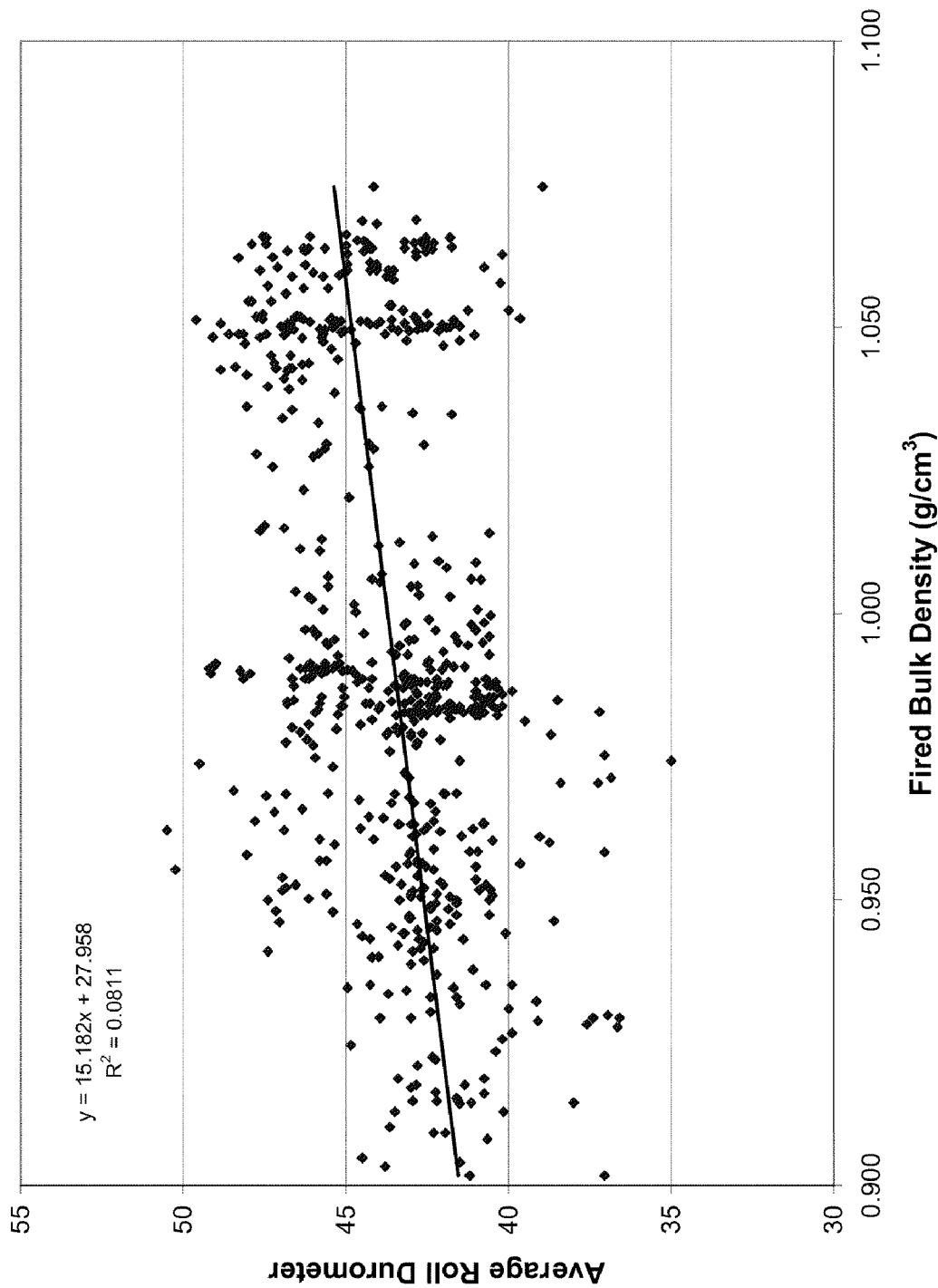
FIG. 5A is a graphical illustration of average Shore D durometer hardness versus fired bulk density for exemplary shorter length pulling rolls.
Figure 5B:
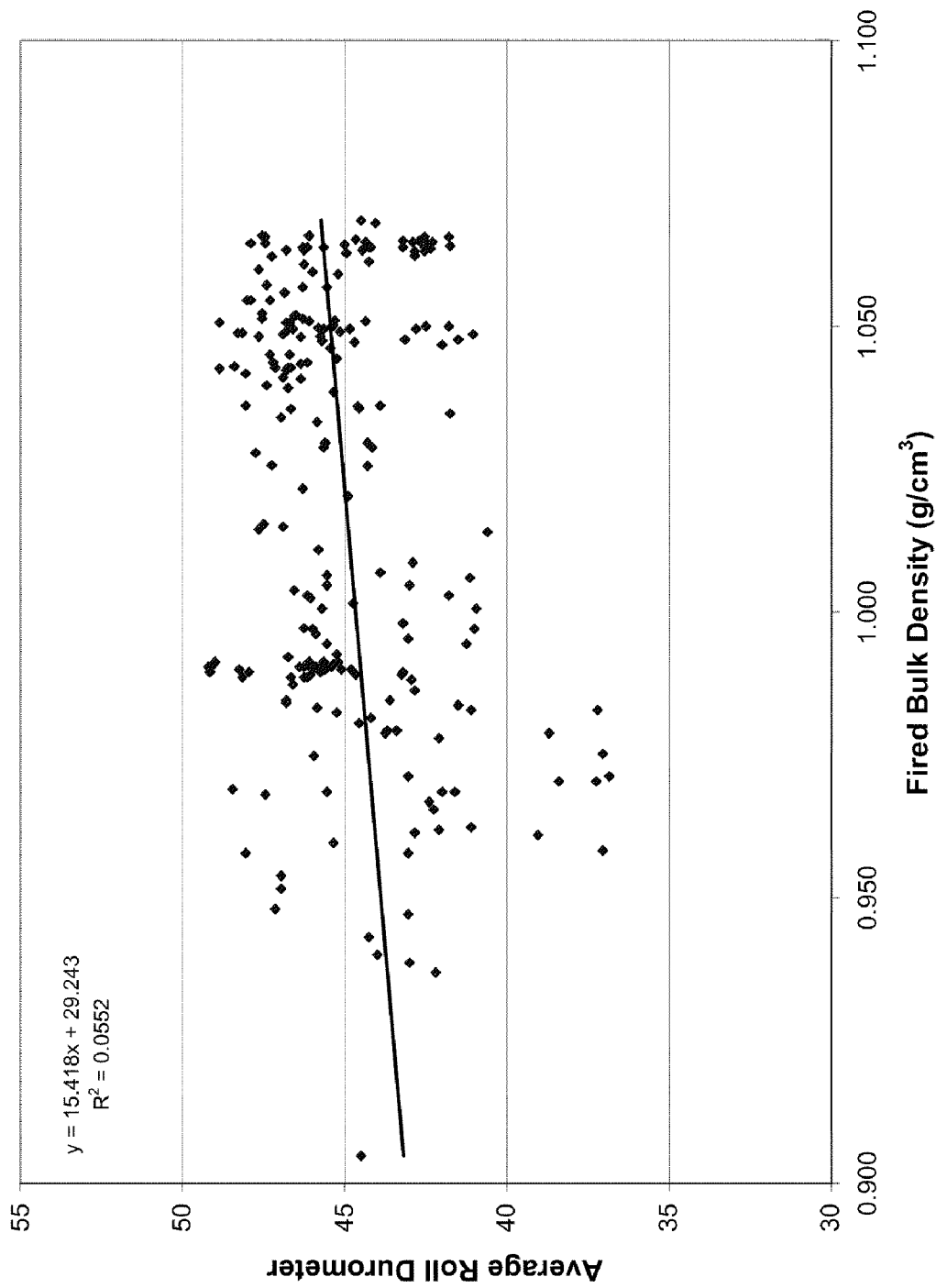
FIG. 5B is a graphical illustration of average Shore D durometer hardness versus fired bulk density for exemplary longer length pulling rolls.
Figure 5C:
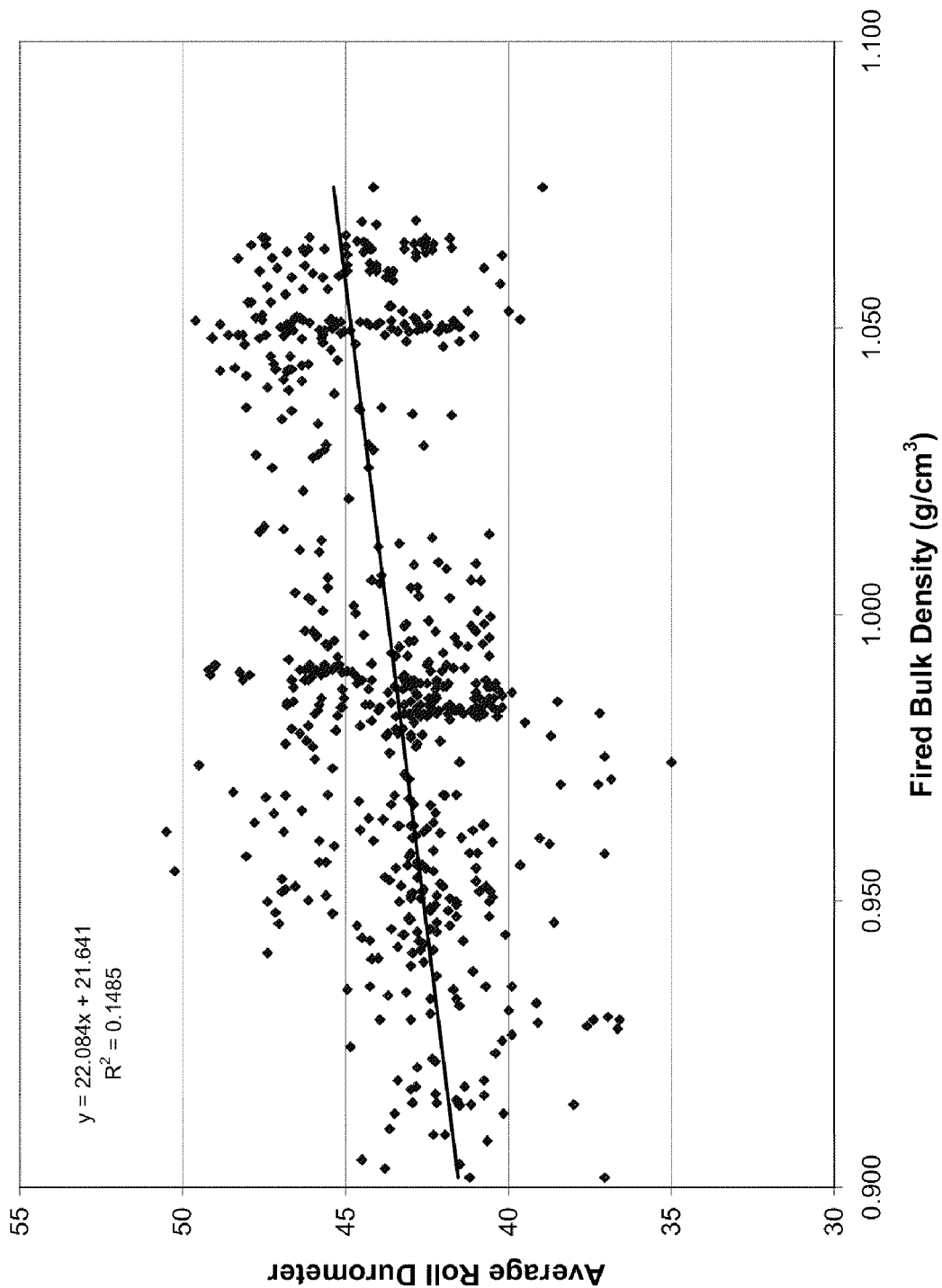
FIG. 5C is a graphical illustration of average Shore D durometer hardness versus fired bulk density for exemplary shorter length and longer length pulling rolls.

Correlation between Shore D Durometer Hardness and Fired Bulk Density of Pulling Rolls FIGS. 5A, 5B and 5C illustrate the correlation between fired bulk density and average durometer hardness. As illustrated in these figures, there is a positive correlation between the variables. However, due to minor errors in measurement when conducting the tests (such as error in measuring the durometer hardness and, to a lesser degree, the weight of the plates), the figures illustrate significant scatter of the data points and degrade the correlation coefficient. In principle, however, the higher the density of the pulling roll (and thus, the tester cartridge), the higher the durometer hardness value. FIG. 5C illustrates a combination of the data shown in FIGS. 5A and 5B, due to the overlap in the range of the average durometer readings in FIGS. 5A and 5B, and demonstrates the more defined correlation between durometer hardness and fired bulk density.

Example 4

Comparison of Shore D Durometer Hardness between Tester Cartridges and Production Pulling Rolls A test was conducted to measure the Shore D durometer hardness of tester cartridges and production pulling rolls made from the same millboard material. As can be seen in Table 1, the values measured using the tester cartridges were substantially similar to those measured on the pulling rolls. In conducting this test, pulling rolls were used with material on each end of the shaft (i.e., the drive end and idle end) and no material in between. Columns "A" and "B" for each end of the shaft represent the respective pulling rolls that are utilized as a pair in the manufacture of sheet glass. As discussed above, pulling rolls are used in pairs and both rolls comprise material from the same lot. The "Overall Average" column provides the average Shore D durometer measurements for the material in the production pulling rolls; whereas the "Tester Average" column provides the average Shore D durometer measurements of testing cartridges produced from the same lot of material. As can be seen, in this particular test, the average Shore D durometer measurement for the production pulling rolls was 42 and the average Shore D durometer measurement for the tester cartridge was 41.

TABLE 1

Comparison of Finished Pulling Rolls from a Given Millboard Lot with Tester Cartridges Using Plates from the Same Lot

| Avg Shore D Durometer | | | | | |
|---|---|---|---|---|---|
| Drive End | | Idle End | | Overall | Tester |
| A | B | C | D | Average | Average |
| 43 | 43 | 41 | 42 | 42 | 41 |
| 43 | 46 | 43 | 41 | 43 | 41 |
| 41 | 41 | 41 | 41 | 41 | 41 |
| 41 | 40 | 41 | 42 | 41 | 41 |

TABLE 1-continued

Comparison of Finished Pulling Rolls from a Given Millboard Lot with Tester Cartridges Using Plates from the Same Lot

| | Avg Shore D Durometer | | | | | |
|---|---|---|---|---|---|---|
| | Drive End | | Idle End | | Overall | Tester |
| | A | B | C | D | Average | Average |
| | 43 | 46 | 42 | 47 | 44 | 41 |
| | 42 | 43 | 42 | 43 | 42 | 41 |
| Avg | 42 | 43 | 42 | 42 | 42 | 41 |

Example 5

Effects of Over-Compression of a Tester Cartridge and the Impact on Shore D Hardness A test was conducted in which the compressed length of the tester cartridges was fixed, rather than being computed for achieving a target bulk density of 1.025 g/cc. As Table 2 demonstrates, the fixed compressed length was shorter (i.e., the cartridges were over-compressed) than needed to achieve the desired target bulk density of 1.025 g/cc. The resulting bulk densities of the over-compressed cartridges were higher than the target bulk density, as represented in the column labeled "Estimated Bulk Density Based on Actual Compressed Length". Columns 1-6 represent measurements taken at three positions along the axis of the cartridge (i.e., left, center and right), and the same three positions after turning the cartridge 180 degrees. As can be seen in the "Average Durometer" column, by over-compressing the cartridges, the durometer hardness values increased (some beyond the specification tolerances of 35-50). Additionally, the values were higher than the average durometer hardness of a production roll from the same lot. One disadvantage of using production rolls that are too hard (i.e., higher than the specification tolerance) is that the rolls will cause checks or other defects in the sheet glass during production.

TABLE 2

Effect of Over-Compressing Cartridges on Durometer Hardness Values
SD115 Material Testing Fired Centers

| | | | | | | DUROMTER Tolerance 35.50 | | | | | | |
|---|---|---|---|---|---|---|---|---|---|---|---|---|
| WEIGHT | Initial Length | Actual Compressed Length | Estimated Compressed Length (p = 1.025 g/cc) | Estimated Bulk Density Based on Actual Compressed Length | Recovered Length | 1 | 2 | 3 | 4 | 5 | 6 | Average Durometer |
| 505 | 7.438 | 5.750 | 5.933 | 1.092 | 6.250 | 49 | 50 | 50 | 45 | 51 | 50 | 49.2 |
| 502 | 7.438 | 5.750 | 5.898 | 1.085 | 6.250 | 46 | 58 | 50 | 48 | 59 | 45 | 51.0 |
| 505 | 7.438 | 5.750 | 5.933 | 1.092 | 6.250 | 49 | 61 | 49 | 55 | 50 | 53 | 52.8 |
| 503 | 7.438 | 5.750 | 5.910 | 1.087 | 6.250 | 48 | 48 | 49 | 56 | 45 | 48 | 49.0 |
| 504 | 7.375 | 5.750 | 5.922 | 1.090 | 6.250 | 56 | 48 | 52 | 47 | 56 | 48 | 51.2 |
| 504 | 7.375 | 5.750 | 5.922 | 1.090 | 6.313 | 48 | 52 | 52 | 55 | 48 | 50 | 50.8 |
| 505 | 7.375 | 5.750 | 5.933 | 1.092 | 6.250 | 40 | 43 | 49 | 49 | 57 | 52 | 48.3 |
| 503 | 7.375 | 5.750 | 5.910 | 1.087 | 6.250 | 54 | 53 | 58 | 45 | 56 | 47 | 52.2 |
| 507 | 7.500 | 5.813 | 5.957 | 1.084 | 6.313 | 50 | 45 | 49 | 48 | 56 | 48 | 49.3 |
| 504 | 7.438 | 5.750 | 5.922 | 1.090 | 6.250 | 47 | 56 | 50 | 55 | 53 | 55 | 52.7 |
| | | | | Avg = | | | | | | | | 50.4 |
| | | | | Production Roll avg (same lot) = | | | | | | | | 45.7 |

As shown in Table 2, the actual compressed lengths are shorter than they should have been, so the determined durometers are higher. Further, the desired bulk density target is preferably about 1.025 g/cc, but, in another example, the bulk densities can vary about 1.09 g/cc.

Example 6

Calculating the Compressed Cartridge Length Needed to Achieve a Predetermined Bulk Density As discussed above, in one embodiment of the present invention, the cartridge may be compressed to a predetermined bulk density, and the compressive force needed to achieve that bulk density can then be quantified. In some embodiments, the predetermined bulk density value can be determined by calculating the compressed cartridge length needed to achieve the target bulk density. Table 3 illustrates the calculations that can be used to calculate the necessary compressed length.

TABLE 3

Calculating Compression Length for the Tester

Where:
$\rho$ = target bulk density = 1.025 g/cm³
r = radius of the filed plates = 3.2258 cm
$V_M$ = volume of test cartridge at compressed length =
W = weight of test cartridge of 30 filed plates =
M = compressed length of the test cartridge to achieve the desired bulk density =
$\rho = w/V_M$, which, solved for $V_L$, yields $V_M = w/\rho$,
also $V_M = \pi r^2 M$
Therefore:
$w/\rho = \pi r^2 M$, which, solved for M yields $M = w/(\rho \pi r^2)$
$M = w/((1.025 \text{ g/cm}^3)(3.14\ldots)(3.23 \text{ cm})^2)$
$M = (w/33.50800821 \text{ g/cm}) \times (1 \text{ in.}/2.54 \text{ cm})$
$M = w (1 \text{ in.})/85.11034086 \text{ g}$
Thus, the equation
$M = w (1 \text{ in.})/85.11 \text{ g}$
is used to find the compressed length. In one example, the compressed length can be calculated by this methodology. It is also contemplated that the operator can also change the target density and the radius of the fired plates as desired.

Example 7

Calculating Cartridge Pressure Needed to Simulate Conditions Applied to Production Pulling Rolls As described above, in one embodiment, properties of cartridges are measured in order to determine whether one lot of material will be suitable for use in the production of pulling rolls. One way of measuring the properties of the cartridge is to simulate the conditions that the pulling rolls undergo when in use. For example, if a pulling roll is subjected to a known pressure when in use, the testing cartridge can be subjected to an analogous pressure in order to measure or determine various properties. In some embodiments, the testing can be of tester cartridges in which the material has been fired. Optionally, the testing can be of tester cartridges in which the material is unfired. In either or both cases, the measurement of material properties (such as, but not limited to, compressibility, recovery and resiliency) can then be compared to vendor-supplied data to determine if the material complies with the necessary specifications. The following formulas demonstrate the calculations needed to simulate 200 psi of pressure on a pulling roll in a system having an 8.625-inch diameter hydraulic ram, on a cartridge in a system having a 2.5-inch diameter hydraulic ram (e.g., piston).

$$F = PA = \text{pressure} * \text{area}$$
$$= (200) * (8.625/2)^2 * \pi$$
$$= 11685 \text{ lbs}$$

In order for the system to match this force on the tester cartridge, the necessary pressure can be calculated by using the diameter of the hydraulic ram on the tester.

$$11685 \text{ lbs} = PA = \text{pressure} * \text{area}$$
$$= P * (2.5/2)^2 * \pi$$
$$P = 2380 \text{ psi}$$

Once the necessary pressure has been calculated, various material properties such as compressibility, recover, and resiliency can be measured, as shown in the formulas below.

Figure 6:
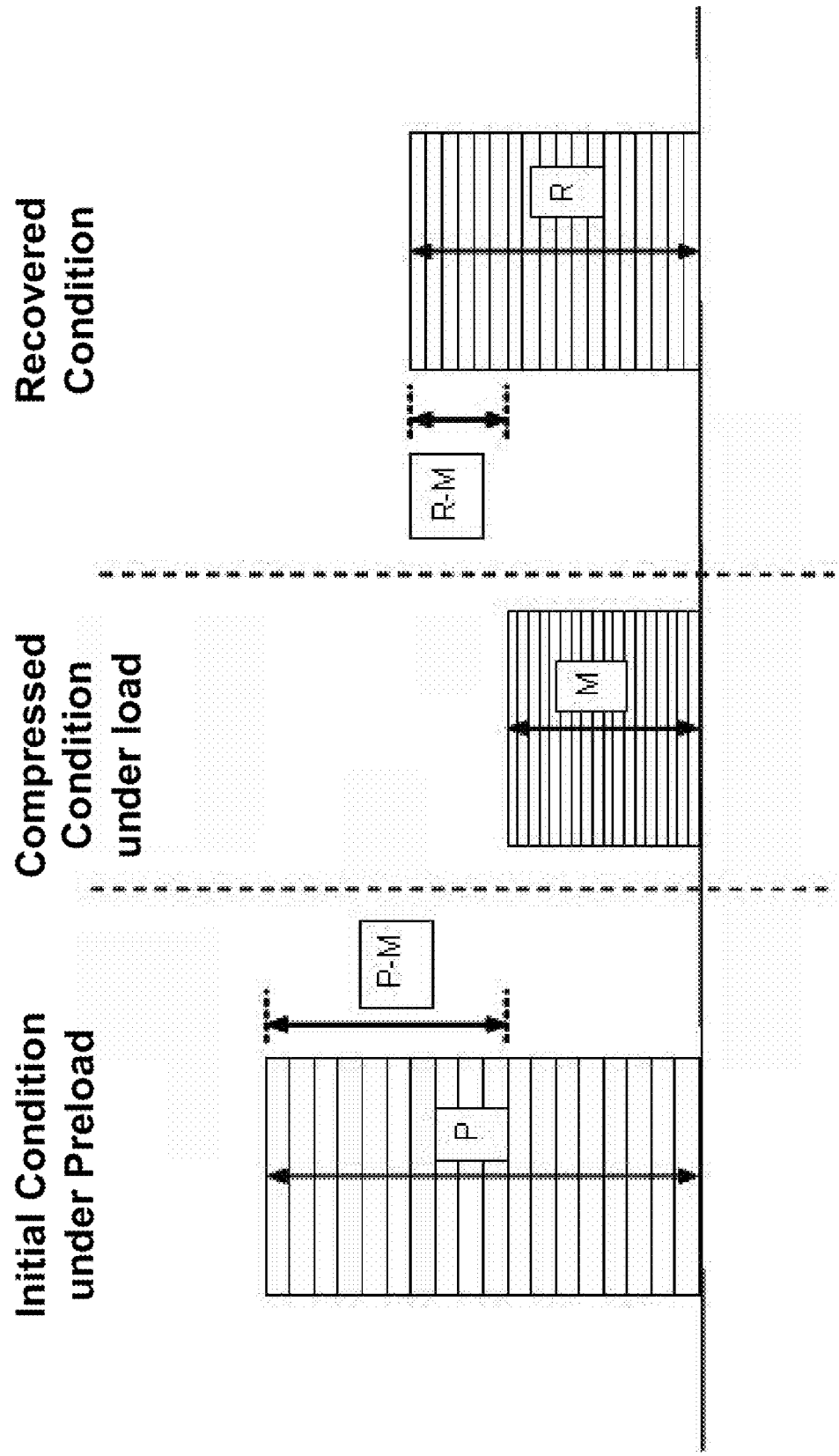
FIG. 6 is an illustration of the dimensions used in calculating compressibility, recovery and resiliency of a cartridge, according to one embodiment of the present invention.

Based on the ASTM F36 procedure, "Standard Test Method for Compressibility and Recovery of Gasket Materials, the compressibility and recovery are calculated as:

$$\text{Compressibility}, \% = \frac{P-M}{P} * 100\%$$

$$\text{Recovery}, \% = \frac{R-M}{P-M} * 100\%$$

where "P" is the thickness of the plates (i.e., the cartridge) under preload (in millimeters or inches), "M" is the thickness under the total load (in millimeters or inches), and "R" is the recovered thickness (in millimeters or inches). These values are illustrated in FIG. 6.

Resiliency can also be calculated using the following formula:

$$\text{Resiliency}, \% = \frac{R-M}{M} * 100\%$$

It is to be understood that the values provided above are for exemplary purposes and embodiments of the invention are not intended to be limited to those values provided.

The invention claimed is:

1. A method of evaluating a performance property of a millboard material for subsequent use to manufacture a pull roll, comprising the steps of:
   (I) providing a millboard material to be evaluated;
   (II) providing a plurality of plates formed from the millboard material;
   (III) coaxially aligning the plurality of plates along a longitudinal axis;
   (IV) applying a compressive force along the longitudinal axis sufficient to form a compressed cartridge; and
   (V) evaluating a performance property of the millboard material provided in step (I) by testing a characteristic of the compressed cartridge formed in step (IV), wherein step (V) is conducted prior to using the millboard material to manufacture a pull roll configured for use in manufacturing sheet glass.

2. The method of claim 1, wherein the compressed cartridge has a predetermined bulk density, said method further comprising the step of quantifying the applied compressive force.

3. The method of claim 1, wherein the compressed cartridge has a compressed length, said method further comprising the step of determining the compressed length of the compressed cartridge.

4. The method of claim 1, wherein the compressed cartridge is substantially cylindrical.

5. The method of claim 1, wherein the plurality of plates comprise the same or substantially similar dimensions.

6. The method of claim 1, wherein the step of providing a plurality of plates further comprises providing the plurality of plates from a single lot of the millboard material.

7. The method of claim 1, wherein the cartridge has at least one external surface substantially parallel to the longitudinal axis, and wherein the method further comprises rotating the cartridge along the longitudinal axis and contacting at least a portion of the external surface with a cutting surface to provide a finished surface.

8. The method of claim 7, further comprising determining at least one durometer hardness value for at least a portion of the at least one external surface of the cartridge.

9. The method of claim 1, wherein the millboard material is unfired.

10. The method of claim 2, wherein the predetermined bulk density is from about 0.90 g/cc to about 1.20 g/cc.

11. The method of claim 1, wherein the plurality of plates comprises from about 20 to about 50 plates.

12. The method of claim 1, wherein the characteristic tested during step (V) comprises a hardness of the compressed cartridge.

13. The method of claim 1, wherein the characteristic tested during step (V) comprises a bulk density of the compressed cartridge.

14. The method of claim 1, wherein the number of plates used to form the compressed cartridge is less than the number of plates used to form the pull roll configured for use in manufacturing sheet glass.

15. A method of evaluating a performance property of a millboard material for subsequent use to manufacture a pull roll, comprising the steps of:
 (I) providing a millboard material to be evaluated;
 (II) providing a plurality of plates formed from the millboard material;
 (III) coaxially aligning the plurality of plates along a longitudinal axis;
 (IV) applying a compressive force along the longitudinal axis sufficient to form a compressed cartridge; and
 (V) evaluating a performance property of the millboard material provided in step (I) by testing a characteristic of the compressed cartridge formed in step (IV), wherein the characteristic tested during step (V) comprises a bulk density of the compressed cartridge.

16. A method of evaluating a performance property of a millboard material, comprising:
 providing a plurality of plates comprising the millboard material;
 coaxially aligning the plurality of plates along a longitudinal axis; and
 applying a compressive force along the longitudinal axis sufficient to form a compressed cartridge,
 wherein the compressed cartridge has a compressed length, said method further comprising the step of determining the compressed length of the compressed cartridge.

17. The method of claim 16, wherein the compressed cartridge has a predetermined bulk density, said method further comprising the step of quantifying the applied compressive force.

18. The method of claim 16, wherein the compressed cartridge is substantially cylindrical.

19. The method of claim 16, wherein the step of providing a plurality of plates further comprises providing the plurality of plates from a single lot of the millboard material.

20. The method of claim 16, wherein the cartridge has at least one external surface substantially parallel to the longitudinal axis, and wherein the method further comprises rotating the cartridge along the longitudinal axis and contacting at least a portion of the external surface with a cutting surface to provide a finished surface.

21. The method of claim 20, further comprising determining at least one durometer hardness value for at least a portion of the at least one external surface of the cartridge.

22. A method of evaluating a performance property of a millboard material for subsequent use to manufacture a pull roll, comprising the steps of:
 (I) providing a single lot of millboard material to be evaluated;
 (II) providing a plurality of plates formed from the single lot of millboard material, wherein the plurality of plates are formed with the same or substantially similar dimensions;
 (III) coaxially aligning the plurality of plates along a longitudinal axis;
 (IV) applying a compressive force along the longitudinal axis sufficient to form a substantially cylindrical compressed cartridge; and
 (V) evaluating a performance property of the single lot of millboard material provided in step (I) by testing a characteristic of the compressed cartridge formed in step (IV), wherein the characteristic is selected from the group consisting of a bulk density and a hardness of the compressed cartridge, wherein step (V) is conducted prior to using the millboard material to manufacture a pull roll configured for use in manufacturing sheet glass.

* * * * *